United States Patent [19]

Hageman et al.

[11] 4,361,513

[45] Nov. 30, 1982

[54] ESTERS OF PENICILLANIC ACID SULFONE

[75] Inventors: David L. Hageman, Colchester; Thomas C. Crawford, Norwich, both of Conn.

[73] Assignee: Pfizer Inc., New York, N.Y.

[21] Appl. No.: 215,215

[22] Filed: Dec. 11, 1980

[51] Int. Cl.³ ............... C07D 499/00; A61K 31/425
[52] U.S. Cl. ............... 260/245.2 R; 424/270; 424/271
[58] Field of Search ............... 260/245.2 R; 424/270

[56] References Cited

U.S. PATENT DOCUMENTS

| 4,241,050 | 12/1980 | Barth | 260/245.2 R |
| 4,256,733 | 3/1981 | Barth | 260/245.2 R |
| 4,272,439 | 6/1981 | Ganguly et al. | 260/245.2 R |
| 4,331,677 | 5/1982 | Foglio et al. | 260/245.2 R |

OTHER PUBLICATIONS

Chem. Pharm. Bull., 27 (5), 1199 (1979).
J. Org. Chem., 44, 1178 (1979).

*Primary Examiner*—Nicholas S. Rizzo
*Attorney, Agent, or Firm*—Charles J. Knuth; James M. McManus; Allen Bloom

[57] ABSTRACT

A process for preparing halomethyl esters of penicillanic acid sulfone, intermediates to beta-lactamase inhibitors, from the corresponding substituted thiomethyl and sulfinylmethyl esters and a halogenating agent. The thiomethyl and sulfinylmethyl esters of penicillanic acid sulfone are useful intermediates.

10 Claims, No Drawings

ESTERS OF PENICILLANIC ACID SULFONE

BACKGROUND OF THE INVENTION

Despite the wide use and acceptance of penicillins and cephalosporins, beta-lactam antibiotics, in combating bacterial infections, there are certain members within the group that are not active against resistant microorganisms because of the organism's ability to produce a beta-lactamase enzyme which reacts with beta-lactam antibiotic to produce products devoid of antibacterial activity. However, certain substances have the ability to inhibit beta-lactamases, and when used in combination with a penicillin or cephalosporin can increase or enhance the antibacterial effectiveness of the antibiotic against certain beta-lactamase producing microorganisms.

West German Offenlegungsschrift No. 2,824,535 published Dec. 14, 1978 teaches that penicillanic acid sulfone is such an effective beta-lactamase inhibitor. In addition, it is taught in said application that certain esters of penicillanic acid sulfone are readily hydrolyzable in vivo giving high blood levels of this beta-lactamase inhibitor. Further, U.K. Patent Application Ser. No. 2,044,255 and Belgian Pat. No. 883,299 also teaches that halomethyl esters of penicillanic acid sulfone can be useful intermediates in the synthesis of readily hydrolyzable esters which degrade in vivo into penicillanic acid sulfone and a beta-lactam antibiotic.

In this latter reference the preferred method for preparing the appropriate halomethyl ester of penicillanic acid sulfone comprises the reaction of a salt of said acid with a dihalomethane. While operable, this method leads to unwanted by-products resulting from the reaction of two moles of the acid with one mole of dihalomethane or, alternately considered, a further reaction of halomethyl ester with a second mole of penicillanic acid sulfone salt.

The present invention relates to a process for the synthesis of halomethyl esters of penicillanic acid sulfone which avoids the above mentioned by-product formation. In addition, the invention further relates to useful intermediates for the instantly claimed process.

Chloromethyl esters of simple acids have been prepared through the reaction of the corresponding acid chloride with formaldehyde in the presence of zinc chloride (J. Am. Chem. Soc., 43, 660 (1921), as well as by the reaction of a free acid with formaldehyde and hydrochloric acid in the presence of zinc chloride (Chem. Abst. 53, 4119fg (1959).

N-Chloromethylphthalimide can be formed by the treatment of N-sulfinylmethylphthalimides with sulfuryl chloride, chlorine or thionyl chloride (Chem. Pharm. Bull., 27, 1199 (1979).

SUMMARY OF THE INVENTION

The present invention is a process for the preparation of a compound of the formula

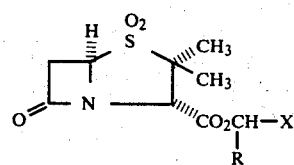

wherein X is chloro, bromo or iodo and R is hydrogen or methyl which comprises reacting a compound of the formula

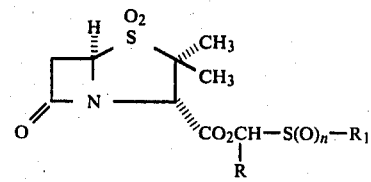

wherein $R_1$ is alkyl of one to six carbon atoms, cycloalkyl of three to eight carbon atoms, benzyl or phenyl and n is an integer of 0 or 1, with a halogenating agent in a reaction inert solvent.

A preferred feature of the claimed process is the use of chlorine, bromine, iodine or oxalyl chloride as the halogenating agent.

A preferred group of compounds employed in the claimed process are those wherein $R_1$ is said alkyl, n is 0 and the halogenating agent is chlorine. Especially preferred are those compounds wherein R is hydrogen and $R_1$ is methyl, and wherein R is hydrogen and $R_1$ is t-butyl.

A second preferred group of compounds for use in the claimed process are those wherein $R_1$ is phenyl, n is 0 and the halogenating agent is chlorine. Especially preferred is that wherein R is hydrogen.

A third preferred group of compounds for use in the claimed process are those wherein $R_1$ is said alkyl, n is 1 and the halogenating agent is chlorine. Especially preferred is that wherein $R_1$ is methyl and R is hydrogen.

The present invention also relates to the intermediates useful as reagents in the claimed process of the formula

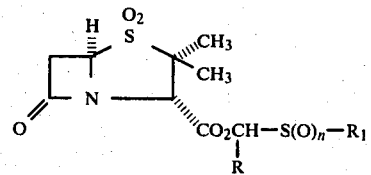

wherein R is hydrogen or methyl, n is an integer of 0 or 1 and $R_1$ is alkyl of one to six carbon atoms, cycloalkyl of three to eight carbon atoms, benzyl or phenyl.

Preferred among these intermediates are those wherein $R_1$ is said alkyl and n is 0. Especially preferred with this group is the compound wherein R is hydrogen and $R_1$ is methyl, and wherein R is hydrogen and $R_1$ is t-butyl.

A second group of preferred intermediates are those wherein $R_1$ is phenyl and n is 0. Especially preferred within this group is the compound wherein R is hydrogen.

A third group of preferred intermediates are those wherein $R_1$ is said alkyl and n is 1. Especially preferred within this group is that intermediate wherein R is hydrogen and $R_1$ is methyl.

As is taught in the art, the coupling of a halomethyl penicillanate sulfone with a simple carboxylic acid salt will result in the formation of an ester readily hydrolyzable in vivo thus providing high blood levels of the desired beta-lactamase inhibitor.

Such an ester, which is readily hydrolyzed in vivo is of the formula

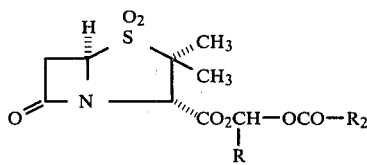

where $R_2$ can be alkyl, aryl, cycloalkyl, aralkyl, alkoxy, heterocyclic and the like.

This same readily hydrolyzable ester can also be prepared by a condensation of a base salt of penicillanic acid sulfone and a halomethyl ester of a carboxylic acid of the formula

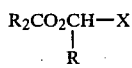

where R and $R_2$ are as previously defined. Accordingly, these halomethyl esters which can be condensed with a base salt of penicillanic acid sulfone can also be prepared by the process of the present invention and which comprises a reaction between a halogenating agent and a thiomethyl or sulfinylmethyl ester depicted as follows:

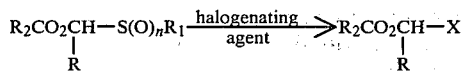

where R, $R_1$, $R_2$, X and n are as previously defined.

DETAILED DESCRIPTION OF THE INVENTION

The process of the present invention is conveniently carried out by reacting a thiomethyl or sulfinylmethyl ester of penicillanic acid sulfone with a halogenating agent. The sulfur containing esters are of the formula

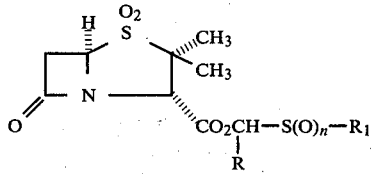

where R, $R_1$ and n are as previously defined, and the halogenating agent can be chlorine, bromine, iodine, oxalyl choride, oxalyl bromide, sulfuryl chloride, phosgene, thionyl chloride, phosphorus pentachloride, phosphorus oxychloride, phosphorus tribromide and phosphorus trichloride.

For each mole of penicillanate sulfone employed it is necessary, for optimum yields, to employ at least one equivalent of the halogenating agent. In most instances it is preferred that a one to two fold excess of the theoretical amount of the halogenating agent be employed.

It is preferred that the claimed process be conducted in a reaction-inert solvent. By such a solvent is meant one which appreciably solubilizes the reactants without reacting to any great extent with the reactants or products under the conditions of the reaction. It is preferred that said solvents have boiling and freezing points compatible with reaction temperatures. Such solvents or mixtures thereof include water immiscible halogenated hydrocarbons such as methylene chloride, chloroform and hexachloroethane and aromatic solvents such as toluene and xylene.

Reaction time is inherently dependent on concentration, reaction temperature and reactivity of the starting reagents. When the reaction is conducted at the preferred reaction temperature of $-30°$ to $25°$ C. the reaction time for the formation of the product is about 10-60 minutes.

On completion of the reaction, the reaction mixture is subjected to an aqueous wash to aid in the removal of unreacted reagents and/or by-products, and the organic phase evaporated to give the desired product.

As previously mentioned, U.K. Patent Application Ser. No. 2,044,255 teaches that the halomethyl penicillanate sulfones, products of the presently claimed process, can be coupled with a variety of beta-lactam antibiotics to provide in vivo antibacterial agents which result from the absorption and subsequent hydrolysis of the coupled product to give high blood and tissue levels of penicillanic acid sulfone and the beta-lactam antibiotic resulting from said hydrolysis. In addition, the aforementioned U.K. application teaches how to use the products resulting from a coupling of penicillanic acid sulfone and a beta-lactam antibiotic.

Also within the scope of the present invention are compounds of the formula

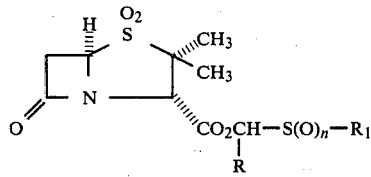

wherein R, $R_1$ and n are as previously defined. These compounds are useful intermediates in the process of the present invention, and are prepared by the hereinafter described method which comprises reacting a base salt, preferably the sodium salt, with a halomethyl sulfide.

In practice, one mole of a base salt of penicillanate sulfone and one mole of the halomethyl sulfide are contacted in a reaction-inert solvent in the presence of a catalytic amount, usually one-tenth of a mole, of a tetraalkylammonium halide, such as tetrabutylammonium bromide or iodide. The catalyst is included to promote formation of the desired product. In addition to the above, a mole of sodium bicarbonate is also added to the reaction mixture.

The criteria for a reaction-inert solvent for the process leading to the aforementioned intermediates are similar to those for the claimed process of the present invention. Said solvents should solubilize the reactants without reacting to any appreciable extent with either the reactants or the product under the conditions of the reaction. It is also preferred that said solvents have boiling and freezing points compatible with the reaction temperature. The preferred solvent for said reaction is acetone, although a wide variety of other water-miscible solvents including dimethylformamide, and hexamethylphosphoramide are also operable.

Reaction time is dependent on concentration, reaction temperature and reactivity of the starting reagents. When the reaction is conducted at the preferred temperature of about 50°-75° C. the reaction is usually substantially complete in 3-4 hours. For convenience, the reaction is frequently allowed to proceed overnight without a detrimental affect on the product.

On completion, the solvent, if it has a relative low boiling point, can be removed in vacuo and the residue partitioned between water and a water immiscible solvent such as methylene chloride. On removal of the organic solvent the product is obtained free of any water soluble materials. If the reaction solvent is high boiling water-miscible solvent the reaction mixture can be quenched in water and the product extracted, as noted above, with a water immiscible solvent such as methylene chloride.

Preparation of those compounds which are intermediates to the claimed process wherein n is 1 is conveniently carried out by oxidation of those compounds wherein n is 0, and comprises reacting one mole of the sulfide (n=0) with one equivalent of an oxidizing agent in a reaction-inert solvent.

While a wide variety of oxidizing agents can be employed in converting the sulfide to a sulfoxide, the preferred agent is m-chloroperbenzoic acid. In order to minimize interaction of the solvent with the oxidizing agent it is preferred that a halogenated hydrocarbon solvent, such as methylene chloride, be employed.

Reaction temperatures are not critical, and the reagents are initially combined at −20° to 0° C. and allowed to warm to room temperature. At these ambient temperatures the reaction is usually complete in about 45-60 minutes.

The acidic by-products of the reaction are removed by a bicarbonate wash of the organic phase, and the product is isolated by concentration of the organic layer.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

Chloromethyl Penicillanate Sulfone

A. methylthiomethyl penicillanate sulfone

A mixture of 15 g. of sodium penicillanate sulfone, 5.04 g. of sodium bicarbonate, 500 mg. of sodium chloride, 2.25 g. of tetrabutylammonium iodide, and 6.95 g. of chloromethyl methylsulfide in 250 ml. of acetone was heated to reflux overnight. The reaction mixture was cooled, evaporated to dryness and taken up in methylene chloride. The organic phase was washed successively with a saturated sodium bicarbonate solution (2×75 ml.), water (1×75 ml.) and a brine solution (1×75 ml.). The organic phase was dried over sodium sulfate and concentrated to give 16.7 g. (95% yield) of the crude product. Recrystallization from methylene chloride/diethyl ether gave 11.7 g. (66% yield), m.p. 128°-131° C.

The NMR spectrum ($CDCl_3$) showed absorption at 1.45 (s), 1.62 (s), 2.27 (s), 3.43 (d), 4.37 (s), 4.60 (t), 5.1 (d) and 5.4 (d) ppm.

B. chloromethyl penicillanate sulfone

To 500 mg. of methylthiomethyl penicillanate sulfone in 25 ml. of methylene chloride cooled to 0° C. and maintained under a nitrogen atmosphere was added with stirring two molar equivalents of chlorine dissolved in methylene chloride. After stirring for 10 minutes the reaction mixture was flushed with nitrogen and the organic phase washed successively with 1 N hydrochloric acid, a saturated sodium bicarbonate solution, water and a brine solution. The organic phase was separated, dried over sodium sulfate and evaporated in vacuo to a foam, 300 mg.

The crude product, 271 mg., was dissolved in ethyl acetate, filtered through silica gel and evaporated to dryness under vacuum to give the product as a yellow oil, 123 mg.

The NMR spectrum ($CDCl_3$) showed absorption at 1.43 (s), 1.60 (s), 3.38 (d), 4.33 (s), 4.53 (t), 5.55 (d) and 5.90 (d) ppm.

EXAMPLE 2

A. Starting with sodium penicillanate sulfone and the appropriate alpha-chloroalkyl alkylsulfide and following the procedure of Example 1A, the following intermediate alkylthiomethyl penicillanate sulfones are prepared:

[Structure diagram of penicillanate sulfone with $CO_2CH(R)-S-R_1$ substituent]

| R | $R_1$ |
|---|---|
| $CH_3-$ | $CH_3-$ |
| $H-$ | $CH_3CH_2-$ |
| $H-$ | $CH_3(CH_2)_2-$ |
| $CH_3-$ | $CH_3(CH_2)_3-$ |
| $H-$ | $CH_3(CH_2)_5-$ |

B. Starting with the indicated alkylthiomethyl penicillanate sulfones (Example 2A) and halogenating agents, and employing the procedure of Example 1B, the indicated haloalkyl penicillanate sulfones are synthesized:

[Scheme: compound I ($CO_2CH(R)-S-R_1$) → halogenating agent → compound II ($CO_2CH(R)-X$)]

| (I) R | $R_1$ | halogenating agent | (II) R | X |
|---|---|---|---|---|
| $H-$ | $CH_3-$ | $Br_2$ | $H-$ | $Br-$ |
| $H-$ | $CH_3$ | $Cl_2$ | $H-$ | $Cl-$ |
| $CH_3-$ | $CH_3-$ | $I_2$ | $CH_3-$ | $I-$ |
| $CH_3-$ | $CH_3-$ | $Cl_2$ | $CH_3-$ | $Cl-$ |
| $H-$ | $CH_3CH_2-$ | $Cl_2$ | $H-$ | $Cl-$ |
| $H-$ | $CH_3CH_2-$ | $Br_2$ | $H-$ | $Br-$ |
| $H-$ | $CH_3(CH_2)_2-$ | $I_2$ | $H-$ | $I-$ |
| $H-$ | $CH_3(CH_2)_2-$ | $Br_2$ | $H-$ | $Br-$ |
| $CH_3$ | $CH_3(CH_2)_3-$ | $Cl_2$ | $CH_3-$ | $Cl-$ |
| $CH_3-$ | $CH_3(CH_2)_3-$ | $Br_2$ | $CH_3-$ | $Br-$ |
| $H-$ | $CH_3(CH_2)_5-$ | $I_2$ | $H-$ | $I-$ |
| $H-$ | $CH_3(CH_2)_5-$ | $Br_2$ | $H-$ | $Br-$ |

-continued

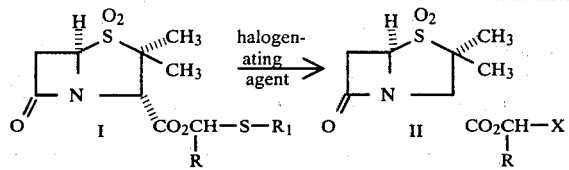

| (I) R | R₁ | halogenating agent | (II) R | X |
|---|---|---|---|---|
| H— | CH₃(CH₂)₅— | Cl₂ | H— | Cl— |

EXAMPLE 3

Chloromethyl Penicillanate Sulfone

A. t-butylthiomethyl penicillanate sulfone

A mixture of 15 g. of sodium penicillanate sulfone, 5.04 g. of sodium bicarbonate, 500 mg. of sodium chloride, 2.25 g. of tetrabutylammonium iodide and 10 g. of chloromethyl t-butylsulfide in 250 ml. of acetone was heated at reflux overnight. The mixture was evaporated in vacuo to dryness and the residue partitioned between 200 ml. of methylene chloride and 200 ml. of water. The organic phase was separated, washed successively with water and a brine solution and dried over sodium sulfate. The solvent was removed under vacuum and the residue dissolved in diethyl ether. On standing the product precipitated from solution and was filtered and dried, 11.0 g. (49% yield), m.p. 85°–87° C.

The NMR spectrum (CDCl₃) showed absorption at 1.41 (s), 1.48 (s), 1.63 (s), 3.45 (d), 4.35 (s), 4.57 (t), 5.23 (d) and 5.50 (d) ppm.

B. chloromethyl penicillanate sulfone

An excess of chlorine gas was gently bubbled into a solution of 200 mg. of t-butylthiomethyl penicillanate sulfone in 20 ml. of methylene chloride cooled to −10° C. After 5 minutes the solution was flushed with nitrogen and concentrated to dryness in vacuo to give the desired product.

EXAMPLE 4

A. Employing the procedure of Example 3A and starting with sodium penicillanate sulfone and the appropriate alpha-chloroalkyl sulfide, the following intermediate thiomethyl penicillanate sulfones are prepared:

| R | R₁ |
|---|---|
| H— | (CH₃)₂CH— |
| CH₃— | (CH₃)₂CH— |
| H— | CH₃CH(CH₃)CH₂— |
| H— | (CH₃CH₂)₂CH— |
| CH₃— | (CH₃CH₂)₂CH— |
| H— | (CH₃CH₂)₂CHCH₂— |
| H— | CH₃(CH₂)₃CH(CH₃)— |
| H— | CH₃(CH₂)₂CH(CH₃)CH₂— |
| CH₃— | (CH₃)₂CHCH(CH₃)CH₂— |

B. Starting with the indicated thiomethyl penicillanate sulfones (Example 4A) and halogenating agents, and following the procedure of Example 3B, the indicated haloalkyl penicillanate sulfones are prepared:

| (I) R | R₁ | halogenating agent | (II) R | X |
|---|---|---|---|---|
| H— | (CH₃)₂CH— | Cl₂ | H— | Cl— |
| CH₃— | (CH₃)₂CH— | Br₂ | CH₃— | Br— |
| CH₃— | (CH₃)₂CH— | Cl₂ | CH₃— | Cl— |
| H— | (CH₃)₃C— | I₂ | H— | I— |
| H— | CH₃CH(CH₃)CH₂— | Cl₂ | H— | Cl— |
| H— | CH₃CH(CH₃)CH₂— | Br₂ | H— | Br— |
| H— | (CH₃CH₂)₂CH— | Cl₂ | H— | Cl— |
| H— | (CH₃CH₂)₂CH— | Cl₂ | H— | Cl— |
| CH₃— | (CH₃CH₂)₂CH— | Cl₂ | CH₃— | Cl— |
| H— | (CH₃CH₂)₂CHCH₂— | I₂ | H— | I— |
| H— | (CH₃CH₂)₂CHCH₂— | Cl₂ | H— | Cl— |
| H— | CH₃(CH₂)₃CH(CH₃)— | Br₂ | H— | Br— |
| H— | CH₃(CH₂)₃CH(CH₃)— | Cl₂ | H— | Cl— |
| H— | CH₃(CH₂)₂CH(CH₃)CH₂— | Cl₂ | H— | Cl— |
| CH₃— | (CH₃)₂CHCH(CH₃)CH₂— | Br₂ | CH₃— | Br— |
| CH₃— | (CH₃)₂CHCH(CH₃)CH₂— | I₂ | CH₃— | I— |

EXAMPLE 5

Bromomethyl Penicillanate Sulfone

A. cyclohexylthiomethyl penicillanate sulfone

A mixture of 15 g. of sodium penicillanate sulfone, 5.04 g. of sodium bicarbonate, 500 mg. of sodium chloride, 2.25 g. of tetrabutylammonium iodide and 11.8 g. of chloromethyl cyclohexylsulfide in 275 ml. of acetone is heated to reflux overnight. The reaction mixture is cooled to room temperature and the solvent subsequently removed in vacuo. The residual material is then partitioned between 200 ml. of methylene chloride and 200 ml. of water. The organic phase is separated, washed with a brine solution and dried over sodium sulfate. Removal of the solvent gives the desired intermediate, which can be further purified by recrystallization from methylene chloride-diethyl ether.

B. bromomethyl penicillanate sulfone

To 616 mg. of cyclohexylthiomethyl penicillanate sulfone in 25 ml. of dry methylene chloride cooled to −15° C. is added 539 mg. of bromine in 15 ml. of methylene chloride, and the reaction mixture allowed to stir in the cold for 30 minutes. The excess bromine is flushed out of the reaction mixture with nitrogen and the residual solution concentrated under vacuum. The residue is triturated several times with diisopropyl ether and is dried in vacuo to give the desired product.

EXAMPLE 6

A. Employing the procedure of Example 5A and starting with the requisite cycloalkylsulfide and sodium penicillanate sulfone, the indicated intermediates are prepared:

B. Employing the indicated thiomethyl penicillanate sulfones (Example 6A) and halogenating agent, and following the procedure of Example 5B, the indicated haloalkyl penicillanate sulfones are prepared:

EXAMPLE 7

Chloromethyl Penicillanate Sulfone

A. phenylthiomethyl penicillanate sulfone

A mixture of 10 g. of sodium penicillanate sulfone, 3.29 g. of sodium bicarbonate, 500 mg. of sodium chloride, 1.44 g. of tetrabutylammonium iodide and 7.39 g. of chloromethyl phenylsulfide in 250 ml. of acetone was heated to reflux overnight. The reaction mixture was cooled and evaporated in vacuo to an oil which was dissolved in methylene chloride and washed successively with a saturated sodium bicarbonate solution, water and a saturated brine solution. The organic phase was separated, dried over sodium sulfate and concentrated to an oil. Trituration of the oil with diethyl ether gave an off white solid, 3.2 g. (74% yield), m.p. 70°–73° C.

The analytical sample was purified by chromatographing on silica gel using ethyl acetate-hexane as the eluent, m.p. 73°–75° C.

Anal. Calc'd. for $C_{15}H_{17}O_5NS_2$: C, 50.7; H, 4.8; N, 3.9. Found: C, 50.7; H, 4.8; N, 3.8.

B. chloromethyl penicillanate sulfone

To 605 mg. of phenylthiomethyl penicillanate sulfone in 30 ml. of methylene chloride cooled to −10° C. and maintained under a nitrogen atmosphere is added two molar equivalents of chlorine dissolved in 25 ml. of methylene chloride. After stirring for 30 minutes the cooling bath is removed and the reaction mixture allowed to warm to room temperature. The reaction mixture is flushed with nitrogen, and the resulting solution washed successively with a saturated sodium bicarbonate solution, water and a brine solution. The organic phase is separated, dried over sodium sulfate and concentrated in vacuo to give the product.

The product is further purified by passing it through a silica gel column using ethyl acetate-hexane (1:1, v:v) as the eluent.

In a similar manner, using the procedures of Example 7A and B, and starting with the appropriate reagents, benzylthiomethyl penicillanate sulfone, phenylthioethylidene penicillanate sulfone are reacted with bromine to give, respectively, bromomethyl penicillanate sulfone and bromoethylidene penicillanate sulfone.

EXAMPLE 8

Chloromethyl Penicillanate Sulfone

A. phenylsulfinylmethyl penicillanate sulfone

To a 3 g. of phenylthiomethyl penicillanate sulfone (Example 7A) in 50 ml. of dry methylene chloride cooled to −20° C. and maintained under a nitrogen atmosphere was added 1.26 g. of m-chloroperbenzoic acid portionwise. The reaction mixture was allowed to stir at room temperature for one hour, at which time an additional 324 mg. of per acid was added. After 30 minutes the reaction solution was washed successively with a saturated sodium bicarbonate solution, water and a brine solution. The organic phase was dried and evaporated to give 2.7 g. of the product as a yellow gum. The product was purified by chromatographing on silica gel using ethyl acetate-hexane (1:1, v:v) as the eluent. The fractions containing the product were combined and concentrated to dryness in vacuo, 1.62 g., m.p. 48° C.

B. chloromethyl penicillanate sulfone

To a solution of 556 mg. of phenylsulfinylmethyl penicillanate sulfone in 25 ml. of methylene chloride cooled to −30° C. and maintained under a nitrogen atmosphere was added 189 mg. of oxalyl chloride in 5 ml. of methylene chloride. The reaction mixture was allowed to warm to room temperature for 60 minutes and was then washed successively with a dilute sodium bicarbonate solution, water and a brine solution. The separated organic phase was dried over sodium sulfate and concentrated to give the product as a white foam.

EXAMPLE 9

A. Employing the procedure of Example 8A, and starting with the appropriate thiomethyl penicillanate sulfones, the following sulfoxides are prepared:

| R | $R_1$ |
|---|---|
| H— | $CH_3$— |
| $CH_3$— | $CH_3$— |
| H— | $CH_3(CH_2)_2$— |
| H— | $(CH_3)_3C$— |
| H— | $(CH_3)_2CH$— |
| $CH_3$— | $(CH_3)_2CH$— |
| $CH_3$— | $(CH_3CH_2)_2CH$— |
| H— | $CH_3(CH_2)_2CH(CH_3)CH_2$— |
| H— | cyclopropyl |
| $CH_3$— | cyclopentyl |
| H— | cyclohexyl |
| $CH_3$— | cyclohexyl |
| H— | cycloheptyl |
| $CH_3$— | $C_6H_5$— |
| H— | $C_6H_5CH_2$— |

B. Starting with indicated sulfinylmethyl penicillanate sulfones and halogenating agent and employing the procedure of Example 8B, the indicated halomethyl penicillanate sulfones are prepared:

| (I) R | $R_1$ | halogenating agent | (II) R | X |
|---|---|---|---|---|
| H— | $CH_3$— | $Cl_2$ | H— | Cl— |
| H— | $CH_3$— | $I_2$ | H— | I— |
| $CH_3$— | $CH_3$— | $(COCl)_2$ | $CH_3$— | Cl— |
| H— | $CH_3(CH_2)_2$— | $Br_2$ | H— | Br— |
| H— | $(CH_3)_3C$— | $Br_2$ | H— | Br— |
| H— | $(CH_3)_2CH$— | $Cl_2$ | H— | Cl— |
| H— | $(CH_3)_2CH$— | $(COCl)_2$ | H— | Cl— |
| $CH_3$— | $(CH_3)_2CH$— | $I_2$ | $CH_3$— | I— |
| $CH_3$— | $(CH_3CH_2)_2CH$ | $Br_2$ | $CH_3$— | Br— |

-continued

| (I) R | R₁ | halogenating agent | (II) R | X |
|---|---|---|---|---|
| H— | CH₃(CH₂)₂CH(CH₃)CH₂— | Cl₂ | H— | Cl— |
| H— | cyclopropyl | Cl₂ | H— | Cl— |
| H— | cyclopropyl | Br₂ | H— | Br— |
| CH₃— | cyclopentyl | Cl₂ | CH₃— | Cl— |
| H— | cyclohexyl | I₂ | H— | I— |
| H— | cyclohexyl | Br₂ | H— | Br— |
| H— | cyclooctyl | Cl₂ | H— | Cl— |
| CH₃— | C₆H₅— | (COCl)₂ | CH₃— | Cl— |
| H— | C₆H₅CH₂— | Cl₂ | H— | Cl— |

We claim:

1. A compound selected from those of the formula

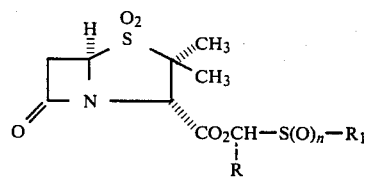

wherein R is selected from the group consisting of hydrogen and methyl, n is an integer of 0 or 1, and $R_1$ is selected from the group consisting of alkyl having from one to six carbon atoms, cycloalkyl having from three to eight carbon atoms, benzyl and phenyl.

2. A compound of claim 1, wherein $R_1$ is alkyl having from one to six carbon atoms and n is 0.

3. The compound of claim 2, wherein R is hydrogen and $R_1$ is methyl.

4. The compound of claim 2, wherein R is hydrogen and $R_1$ is t-butyl.

5. A compound of claim 1, wherein $R_1$ is phenyl and n is 0.

6. The compound of claim 5, wherein R is hydrogen.

7. A compound of claim 1, wherein $R_1$ is alkyl having from one to six carbon atoms and n is 1.

8. The compound of claim 7, wherein R is hydrogen and $R_1$ is methyl.

9. A compound of claim 1, wherein $R_1$ is phenyl and R is hydrogen.

10. The compound of claim 9, wherein n is 1.